United States Patent
Schreck et al.

(10) Patent No.: US 8,781,554 B2
(45) Date of Patent: Jul. 15, 2014

(54) METHOD AND SYSTEM OF SIMULATING MAGNETIC RESONANCE IMAGING SIGNALS

(75) Inventors: Oliver Schreck, Barcelona (ES); Rui Zhang, Shenzhen (CN); Shi Gang Zhang, Shenzhen (CN); Hai Yan Zhou, Shenzhen (CN)

(73) Assignee: Siemens Aktiengesellschaft, München (DE)

( * ) Notice: Subject to any disclaimer, the term of this patent is extended or adjusted under 35 U.S.C. 154(b) by 328 days.

(21) Appl. No.: 13/116,155

(22) Filed: May 26, 2011

(65) Prior Publication Data
US 2012/0043964 A1   Feb. 23, 2012

(30) Foreign Application Priority Data

May 31, 2010   (CN) .......................... 2010 1 0192721

(51) Int. Cl.
  *G01R 33/50* (2006.01)
  *G01R 33/58* (2006.01)
  *A61B 5/055* (2006.01)
  *G01R 33/54* (2006.01)

(52) U.S. Cl.
  CPC ............ *G01R 33/543* (2013.01); *G01R 33/546* (2013.01); *G01R 33/50* (2013.01); *G01R 33/58* (2013.01); *A61B 5/055* (2013.01)
  USPC ............ 600/416; 324/309; 324/307; 324/318

(58) Field of Classification Search
  USPC .......................... 324/300–322; 382/128–131; 600/407–435
  See application file for complete search history.

(56) References Cited

U.S. PATENT DOCUMENTS

| | | | | |
|---|---|---|---|---|
| 3,394,300 | A * | 7/1968 | Packard et al. | 324/310 |
| 6,937,014 | B2 * | 8/2005 | Sun et al. | 324/303 |
| 7,468,605 | B2 * | 12/2008 | Yu et al. | 324/309 |
| 8,143,890 | B2 * | 3/2012 | Dong et al. | 324/309 |
| 2004/0189296 | A1 * | 9/2004 | Sun et al. | 324/306 |
| 2006/0104902 | A1 * | 5/2006 | Powis et al. | 424/9.1 |
| 2007/0247153 | A1 * | 10/2007 | Yu et al. | 324/309 |
| 2010/0004909 | A1 | 1/2010 | Nitz | |
| 2012/0043964 | A1 * | 2/2012 | Schreck et al. | 324/309 |
| 2012/0197105 | A1 * | 8/2012 | Mezer et al. | 600/410 |

OTHER PUBLICATIONS

H. Benoit-Cattin et. al.: "Magnetic Resonance Imaging (MRI) Simulation on a Grid Computing Architecture", Proceedings of the 3rd IEEE/ACM Int. Symposium on Cluster Computing and the Grid, p. 1-6, 2003.

\* cited by examiner

*Primary Examiner* — Melissa Koval
*Assistant Examiner* — Tiffany Fetzner

(57) ABSTRACT

A method for simulating magnetic resonance signals is proposed. A lattice array where each point in the array has several magnetic resonance sensitive particles is provided. Statistic property of each point is set. A raw magnetic resonance imaging data is calculated based on statistic property of each point and a magnetic resonance imaging sequence to be applied. A system for simulating magnetic resonance signals is further proposed. By considering statistic property of each point, it can distinguish every part of the object to be scanned and really reflect the structure of object without using a real magnetic resonance imaging device. It saves time and costs for avoiding several scanning by the real a magnetic resonance imaging device.

10 Claims, 1 Drawing Sheet

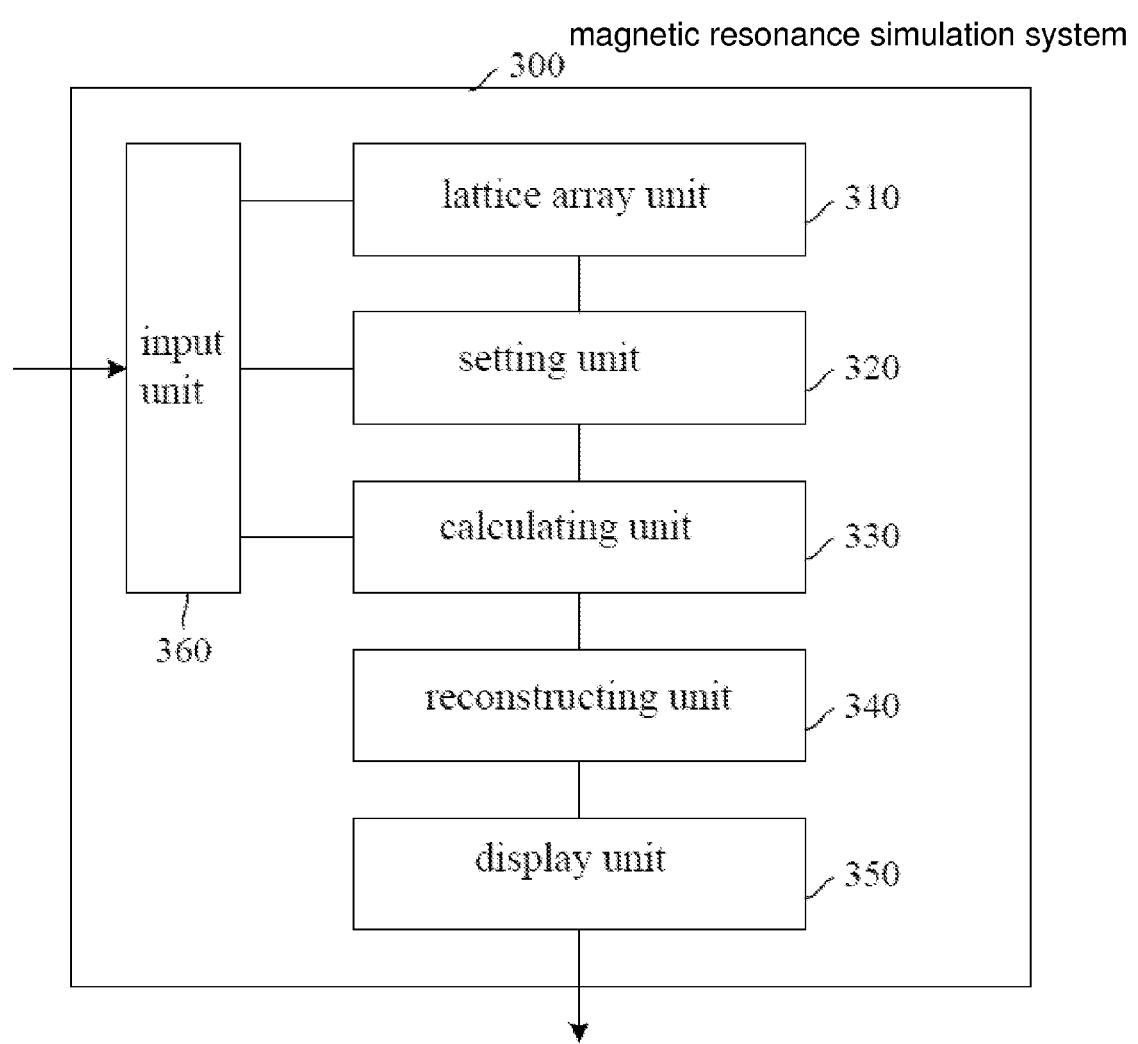

METHOD AND SYSTEM OF SIMULATING MAGNETIC RESONANCE IMAGING SIGNALS

CROSS REFERENCE TO RELATED APPLICATIONS

This application claims priority of Chinese application No. 201010192821.9 filed May 31, 2010, which is incorporated by reference herein in its entirety.

FIELD OF THE INVENTION

The present invention relates to the technical field of magnetic resonance imaging (MRI) and, particularly, to a method for simulating magnetic resonance imaging signals and a system for simulating magnetic resonance imaging signals.

BACKGROUND OF THE INVENTION

There is a need to test a newly developed sequence during the development of the sequences for use in magnetic resonance imaging. Usually, people involved in development efforts need to have an object (a volunteer or a phantom) scanned for many times using a new sequence on real magnetic resonance imaging equipment, so as to accomplish the tests of the new sequence. Since each scan needs from several minutes to a few dozens of minutes, the abovementioned test procedure would take a lot of time due to the numerous scans. Furthermore, carrying out the numerous scans on real magnetic resonance imaging equipment would also lead to high costs.

In the U.S. Patent Application U.S. 20100004909A1, a method and a system for simulating a magnetic resonance image of an examination subject are disclosed. However, in U.S. 20100004909A1, it does not particularly describe how to realize the simulation, and in this patent application the examination subject is treated as an anatomically whole subject and the internal structure of the examination subject (e.g. the white and grey matters of a brain) cannot be fully distinguished, therefore the results of the magnetic resonance imaging cannot be thoroughly simulated, nor the structure of the examination subject be faithfully reflected.

SUMMARY OF THE INVENTION

In view of this situation, the present invention proposes a method for simulating magnetic resonance imaging signals so as to faithfully reflect the structure of an object to be scanned The present invention further proposes a system for simulating magnetic resonance imaging signals.

Therefore, the present invention provides a method for simulating magnetic resonance imaging signals, which method comprises:
  providing a lattice array according to an object to be scanned, each point in the lattice array comprising a plurality of particles sensitive to magnetic resonance;
  setting the statistic properties of each point; and
  calculating raw data for magnetic resonance imaging on the basis of the statistic properties of each point and a magnetic resonance imaging sequence to be applied thereto.

In an embodiment of the abovementioned solution, the step of setting the statistic properties comprises setting each point's longitudinal relaxation time and transverse relaxation time.

In an embodiment of the abovementioned solution, the method further sets the particle density at each point according to the object to be scanned.

An embodiment of the method further comprises setting the gyromagnetic ratio of said particles at each point.

An embodiment of the method further comprises reconstructing a magnetic resonance image on the basis of said raw data.

The present invention further provides a system for simulating magnetic resonance imaging signals, which system comprises:
  a lattice array unit for providing a lattice array according to an object to be scanned, each point in the lattice array comprising a plurality of particles sensitive to magnetic resonance;
  a setting unit for setting the statistic properties of each point in said lattice array; and
  a calculating unit for calculating raw data for magnetic resonance imaging on the basis of the statistic properties of each point and a magnetic resonance imaging sequence to be applied thereto.

According to an embodiment, said setting unit comprises a first setting subunit for setting each point's longitudinal relaxation time and transverse relaxation time.

According to an embodiment, said setting unit further comprises a second setting subunit for setting the particle density at each point according to the object to be scanned; and/or a third setting subunit for setting the gyromagnetic ratios of said particles at each point.

An embodiment of the system further comprises a reconstructing unit for reconstructing a magnetic resonance image on the basis of said raw data.

It can be seen from the abovementioned solutions that since the present invention takes the statistic properties of each point into consideration, it is capable of distinguishing various composing parts of the object to be scanned and faithfully reflecting the structure of the object to be scanned without using real MRI equipment. Furthermore, since the present invention avoids the use of real MRI equipment in carrying out numerous scans, it saves both time and costs.

BRIEF DESCRIPTION OF THE DRAWINGS

Figure is a schematic diagram of the structure of a system according to the present invention.

DETAILED DESCRIPTION OF THE INVENTION

For better understanding of the objects, technical solutions and advantages of the present invention, the present invention will be further described in detail below by way of embodiments.

Each particle (e.g. the atomic nucleus of a hydrogen atom) sensitive to magnetic resonance has its unique property in the magnetic field. The magnetization intensity of a particle can be described as a vector (Mx, My, Mz), and when a main magnetic field (B0 field) is applied thereto, the magnetization intensity of the particle tends to align in the direction along the B0 field (the direction of the Z axis). When a radio frequency (RF) field B1 is applied thereto, the magnetization intensity of the particle deviates from the Z axis, and then has precessions about the Z axis. The abovementioned process of the magnetization intensity deviating from the Z axis can be described as a spin, as shown in Equation (1).

$$\begin{pmatrix} M_{x+} \\ M_{y+} \\ M_{z+} \end{pmatrix} = R \cdot \begin{pmatrix} M_{x-} \\ M_{y-} \\ M_{z-} \end{pmatrix} \quad (1)$$

In which the plus sign "+" represents after an RF pulse has been applied thereto, the subtraction sign "−" represents before the RF pulse is applied thereto, and R is a spin matrix.

After the magnetization intensity has deviated from the Z axis, the transverse projection of the magnetization intensity (the projection on the XY plane) would spin about the Z axis, and would send out magnetic resonance signals. If a gradient field (the phase encoding gradient) is applied thereto, then particles at the different positions would have different frequencies, and the corresponding magnetic resonance signals would accumulate to form different phases during the spin process. Assuming that the position of a particle is $\vec{r}$, then after a time period of t, the magnetic resonance signal sent out by this particle would be as shown in Equation (2).

$$s(\vec{r},t) = M_{\perp}(t) = M_{\perp}(t_0) e^{i\gamma \vec{G} \cdot \vec{r}(t-t_0)} \quad (2)$$

In which $M_{\perp}(t_0)$ is the transverse magnetization intensity at time $t_0$ (when the precession starts after the magnetization intensity has deviated from the Z axis), and it can be decomposed as $M_{\perp}(t_0) = M_x + iM_y$, wherein $M_x$ and $M_y$ are the projections of the transverse magnetization intensity on the X axis and Y axis, and γ is the gyromagnetic ratio of the particle.

If a readout gradient is applied thereto at this moment, then the magnetic resonance signal of the particle is acquired by an analog-to-digital converter (ADC), and stored as raw data. Then a magnetic resonance image can be obtained by performing a Fourier transform (FT) to these raw data or treating them in other ways.

The inventors of the present invention propose a method for simulating magnetic resonance imaging signals on the basis of the abovementioned analysis. In the present invention, it is not a particle that is simulated, but instead it is a "point" at a certain position in the object which is simulated. According to the resolution requirements of the object to be scanned, said point can be very small, but it still contains a large number of particles. A real object to be scanned, such as the head of a person, can be treated as a three-dimensional lattice array. Therefore, the object to be scanned not only has the characteristics of a single particle described above (such as the gyromagnetic ratio) but also has statistic properties such as longitudinal relaxation time T1, transverse relaxation time T2, etc. Therefore, the signal in Equation (2) becomes:

$$s(\vec{r},t) = M_{\perp}(t) = M_{\perp}(t_0) e^{-\frac{t}{T_2}} e^{i\gamma \vec{G} \cdot \vec{r}(t-t_0)} \quad (3)$$

Also, the component of the magnetization intensity in the direction of the Z axis recovers with time:

$$M_z(t) = M_z(t_0) e^{-\frac{t}{T_1}} + M_0 \left(1 - e^{-\frac{t}{T_1}}\right) \quad (4)$$

In which $M_0$ is an initial magnetization intensity.

After a certain time period, a second RF pulse, a phase encoding gradient and a readout gradient are applied thereto according to the sequence, and the magnetic resonance signals (raw data) are acquired, and then the abovementioned procedure is repeated until the magnetic resonance signals of one slice have been acquired.

In particular, the method provided by the present invention comprises the steps as follows:

Step 110: A lattice array (a two-dimensional lattice array or a three-dimensional lattice array, with a three-dimensional lattice array being taken as an example here) is provided according to an object to be scanned, and this three-dimensional lattice array simulates the object to be scanned, with each point in the lattice array comprising a plurality of particles sensitive to magnetic resonance.

By way of example, if the object to be scanned is of a sphere shape (e.g. the head of a person), then a three-dimensional lattice array filled with a corresponding sphere is provided in this step. Preferably, the distances between the points in various directions are the same.

Step 120: The statistic properties of each point in the abovementioned lattice array are set, such as the longitudinal relaxation time T1, the transverse relaxation time T2, etc.

Usually, the number of the particles at each point is different, but the points simulating the same part (e.g. the white matter of a brain) generally have the same number of particles, and the points simulating different parts (e.g. the white matter and the grey matter of a brain) generally have different numbers of particles. Therefore, the particle density at each point can be further set according to the object to be scanned which is thus simulated.

In this step, the gyromagnetic ratios of the particles can be further set. A default gyromagnetic ratio of the particles can also be set beforehand, and this default gyromagnetic ratio is employed in this procedure.

Step 130: Raw data for magnetic resonance imaging are calculated according to Equation (3) on the basis of the statistic properties of each point set above and a magnetic resonance imaging sequence to be applied thereto. Said sequence usually includes RF pulses, a slice selection gradient, a phase encoding gradient, and a readout gradient.

Step 140: A magnetic resonance image is reconstructed by way of a Fourier transform or other ways on the basis of the raw data obtained in the above step. Said magnetic resonance image can be used by people involved in the development of the sequence to judge whether the sequence is appropriate.

As shown in figure, the present invention further provides correspondingly a system 300 for simulating magnetic resonance imaging signals. The system 300 comprises a lattice array unit 310, a setting unit 320 and a calculating unit 330. In the system, the lattice array unit 310 is used for providing a lattice array according to an object to be scanned, and in the lattice array each point contains a plurality of particles sensitive to magnetic resonance. The setting unit 320 is used for setting the statistic properties of each point in the lattice array. The calculating unit 330 is used for calculating raw data for magnetic resonance imaging on the basis of the statistic properties of each point and a magnetic resonance imaging sequence to be applied thereto.

The lattice array unit 310, the setting unit 320 and the calculating unit 330 can directly receive information input by an operator from outside the system, such as the lattice array information, the statistic properties of the points, the magnetic resonance sequence, etc. Alternatively, the system 300 can also comprise an input unit 360 for receiving information from outside (for example, the input by an operator) required by the abovementioned lattice array unit 310, setting unit 320 and calculating unit 330, and then transmit the same to the lattice array unit 310, setting unit 320 and calculating unit 330, respectively. The input unit 360 can be conveniently realized by a commonly used input device such as a keyboard, a mouse, etc.

In the system 300 as shown in figure, the setting unit 320 can comprise a first setting subunit (not shown in the figure), which first setting subunit is used for setting each point's longitudinal relaxation time and transverse relaxation time. The setting unit 320 can further comprise a second setting subunit (not shown in the figure), which is used for setting the particle density at each point according to the simulated object to be scanned. The setting unit 320 can further comprise a third setting subunit for setting the gyromagnetic ratios of the particles at each point.

The system 300 can further comprise a reconstructing unit 340, which is used for reconstructing a magnetic resonance image on the basis of the raw data. Furthermore, the system 300 can comprise a display unit 350, which display unit 350 is used for displaying the magnetic resonance image reconstructed by the reconstructing unit 340.

As to the operating process of the system 300, reference can be made to the previous descriptions of the method.

According to the present invention, it does not need to use real magnetic resonance imaging equipment, therefore it improves the operating speed and significantly reduces the time and costs spent. Also, since it does not need to use real magnetic resonance imaging equipment, the whole process is safer. Compared to the prior art in which the macroscopic object as the object to be scanned is treated as a whole and signals are obtained by means of the Fourier transform, the present invention uniquely simulates the object to be scanned as a lattice array, and simulates the characteristic statistic properties of each point, so as to obtain the faithful magnetic resonance imaging signals of the object to be scanned. By way of the abovementioned technology of the present invention, the faithful characteristics of an object to be scanned under the magnetic resonance, such as a magnetic resonance phantom or some living organisms of a human body and the like, can be well represented.

The present invention not only can be used to check the magnetic resonance sequences, but also can be used to examine the quality of an image and to analyze magnetic resonance signals and so on.

What are described above are merely preferred embodiments of the present invention, and are not to limit the present invention, and any modification, equivalent and improvement within the spirit and principles of the present invention shall be covered in the protective scope of the present invention.

The invention claimed is:

1. A method that simulates magnetic resonance imaging signals, comprising:
    simulating an object to be scanned as a two-dimensional or a three-dimensional lattice array using a lattice array unit, with each point in the lattice array comprising:
        a plurality of magnetic resonance sensitive particles;
    simulating a statistic property of each point in the lattice array by a setting unit; and
    calculating raw data of a simulated magnetic resonance image without using a real magnetic resonance imaging scanner in order to perform a plurality of simulated magnetic resonance imaging sequence scans,
    wherein the raw data is calculated, with a calculating unit, based only on the simulated statistic property of each point in the lattice array and the performed plurality of simulated magnetic resonance imaging sequence scans applied by said calculating unit,
    wherein the statistic property of each point in the lattice array is simulated by setting a longitudinal relaxation time and a transverse relaxation time of each point in the lattice array.

2. The method as claimed in claim 1, wherein the simulated magnetic resonance imaging sequence scans applied comprise:
    radiofrequency pulses, a slice selection gradient, a phase encoding gradient, and a readout gradient.

3. The method as claimed in claim 1, wherein a particle density at each point in the lattice array is set based on the object that is being imaged by simulation.

4. The method as claimed in claim 1, wherein a particle gyromagnetic ratio, at each point in the lattice array, is set.

5. The method as claimed in claim 1, further comprising reconstructing the simulated magnetic resonance image based on the calculated raw data and displaying the simulated magnetic resonance image on a display unit.

6. A system that simulates a magnetic resonance imaging signals, comprising:
    a lattice array unit configured for simulating an object to be scanned as a two-dimensional or a three-dimensional lattice array using a lattice array unit, with each point in the lattice array comprising:
        a plurality of magnetic resonance sensitive particles;
    a setting unit configured for simulating a statistic property of each point in the lattice array; and
    a calculating unit configured for calculating raw data that is usable in simulating a magnetic resonance image without using a real magnetic resonance imaging scanner in order to perform a plurality of simulated magnetic resonance imaging sequence scans,
    wherein the raw data is calculated based only on the simulated statistic property of each point in the lattice array and the performed plurality of simulated magnetic resonance imaging sequence scans applied by said calculating unit;
    wherein the statistic property of each point in the lattice array is simulated by setting a longitudinal relaxation time and a transverse relaxation time of each point in the lattice array.

7. The system as claimed in claim 6, wherein the simulated magnetic resonance imaging sequence scans applied comprise:
    radiofrequency pulses, a slice selection gradient, a phase encoding gradient, and a readout gradient.

8. The system as claimed in claim 6, further comprising:
    a second setting unit configured for setting a particle density at each point in the lattice array based on the object that is being imaged by simulation and
    a third setting unit configured for setting a particle gyromagnetic ratio at each point in the lattice array.

9. The system as claimed in claim 6, further comprising:
    an input unit configured for receiving and transmitting information from the lattice array unit, the setting unit, and the calculating unit.

10. The system as claimed in claim 6, further comprising:
    a reconstructing unit configured for reconstructing a simulated magnetic resonance image based on the calculated raw data and a display unit configured for displaying the simulated magnetic resonance image.

* * * * *